United States Patent [19]

Keene et al.

[11] 4,176,959

[45] Dec. 4, 1979

[54] HIGH GAIN LASER SPECTROMETER

[75] Inventors: Wayne H. Keene, Medfield; Robert I. Rudko, Holliston; Charles M. Sonnenschein, Brookline, all of Mass.

[73] Assignee: Raytheon Company, Lexington, Mass.

[21] Appl. No.: 897,062

[22] Filed: Apr. 17, 1978

[51] Int. Cl.² .................... G01J 3/42; G01N 21/04
[52] U.S. Cl. ............................. 356/325; 356/327; 356/408; 356/425
[58] Field of Search .............. 356/319, 320, 323, 325, 356/326, 328, 402, 408, 425, 434, 435, 437, 438

[56] References Cited

U.S. PATENT DOCUMENTS

| 3,805,074 | 4/1974 | McCormack | 250/355 |
| 3,843,258 | 10/1974 | Shupe | 356/88 |
| 3,856,406 | 12/1974 | Noble et al. | 356/106 S |
| 3,950,100 | 4/1976 | Keene et al. | 356/28 |
| 4,012,145 | 3/1977 | Chabannes et al. | 356/320 |

Primary Examiner—Vincent P. McGraw

Attorney, Agent, or Firm—David M. Warren; Joseph D. Pannone; Milton D. Bartlett

[57] ABSTRACT

A spectrometer for measuring the spectra and concentration of airborne chemicals at long ranges wherein the optical signals may be occluded by dust. A single lasing medium is utilized both for producing a transmitted optical signal and for amplifying a received optical signal, the frequencies of radiation of the transmitted and received optical signals being offset as the radiation propagates to a distant reflector and back to the lasing medium. The frequency offset is obtained by sweeping the transmitted frequency at a rate commensurate with the round trip propagation time whereby the offset is sufficient to place the received frequency at a peak at the amplifying spectrum of the lasing medium. A laser containing the laser medium further incorporates an interferometric structure within the optical path for sequentially shifting the frequency of oscillation to produce a comb spectrum for sampling the spectra of the chemicals to provide identifying signatures thereof.

13 Claims, 4 Drawing Figures

HIGH GAIN LASER SPECTROMETER

BACKGROUND OF THE INVENTION

Infrared spectroscopy has been utilized for identifying gaseous reagents within a confined region such as a test chamber for comparing the spectrum of the gaseous reagents with the spectrum of a known gas in a reference chamber. Typically, a laser is operated to produce various spectral lines within the region of the expected absorption spectra of the unknown gaseous reagents such that the amplitudes of the observed spectrum can be correlated or compared with the spectra of known chemicals to identify the unknown reagent. The laser spectrometers may be configured to provide for a reference signal to aid in the reception of the optical signal radiation from the test chamber to permit a heterodyning of a received frequency with the reference frequency to produce a beat frequency signal which is readily processed electronically for identifying the frequency and amplitude of the beat frequency signal. One such arrangement is disclosed in the U.S. Pat. No. 3,856,406 which issued in the name of Noble et al. on Dec. 24, 1974.

A problem arises in the obtaining of identifying spectral signatures of chemicals at a long distance, through the air, such as airborne gaseous reagents a number of miles away from the spectrometer. Difficulties exist because of the ever present dust particles or rain drops suspended within the air along the optical path via which the optical radiation must propagate between the spectrometer and the unknown chemicals. The dust or water may attenuate the received signal to the point where an accurate identification of the unknown chemicals is impossible in the absence of a very high gain receiver for the received signal at the spectrometer. An amplifying medium of suitable gain for the aforementioned situation is the medium of an oscillating laser such as that disclosed in the U.S. Pat. No. 3,950,100 which issued in the name of Keene et al, on Apr. 13, 1976 which teaches that a power gain, even higher than the gain of the laser at the frequency of oscillation can be obtained at a frequency offset therefrom by approximately 250 kilohertz (kHz). The gain at the frequency of oscillation is reduced from that of the offset frequency, in the case of a carbon dioxide laser, by a carbon dioxide depletion region, the depletion region being absent at the 250 kHz frequency offset. The gain provided by such a lasing medium is substantially higher than that which can be obtained by a lasing medium which has not been excited to the point of oscillation. However, the restriction to a specific frequency offset, required for the high gain amplification is not compatable with the teaching of Nobel wherein differing frequency offsets are utilized as an indication of a specific spectral line.

SUMMARY OF THE INVENTION

The aforementioned problems are overcome and other advantages are provided by a laser spectrometer which, in accordance with the invention, utilizes a common lasing medium for the generation of both the transmitted optical radiation and the received optical radiation. A lens system is provided for directing a beam of optical radiation from the lasing medium to a distant reflector, such as a rock on a hillside, from which the optical radiation is reflected back to the lasing medium. The lasing medium provides amplification of the radiation power to a suitable level to permit the amplified received signal to be heterodyned with a reference signal. A frequency offset between the transmitted and received optical signals is provided by a sawtooth, or chirp, frequency modulation which is continuously present during the transmission of the optical radiation. The rate of frequency modulation is adjusted to be commensurate with the radiation propagation time between the lasing medium and the distant reflector such that the frequency offset accumulated during the round trip propagation time is of the desired value to produce the maximum amplification of the received radiation by the lasing medium.

In order to produce a succession of spectral lines for sampling the spectrum of an unknown chemical, such as a gaseous reagent which may be blown into the optical path by the wind, an interferometric structure is positioned within the optical path of a laser incorporating the aforementioned lasing medium for successively altering the frequencies of the transmitted radiation to produce a sequence of radiated frequencies, each of these frequencies serving as a sample point of the unknown spectrum.

In a preferred embodiment of the invention utilizing a carbon dioxide laser, the chirp frequency modulation is provided by a cadmium telluride crystal wherein the optical radiation passes along an axis thereof while a voltage having a ramp waveform is applied transversely to the axis of the crystal. The propagation speed of the radiation in the crystal varies with the magnitude of the applied voltage, so that, as the voltage is varied linearly with time, the propagation speed varies linearly with time to produce the aforementioned chirp frequency modulation. The interferometric structure is accomplished by means of a set of parallel ruled lines upon one of the end mirrors of the laser, the mirror being tilted at an angle of approximately 20° from a perpendicular orientation to the optical path so that a maximum intensity of the interferometric radiation pattern is directed along the optical axis of the laser at the specific frequency for which oscillation is desired. Tilting of the ruled mirror shifts the oscillation frequency to another oscillatory band wherein oscillation occurs. As the modulation frequency is offset linearly with time, the aforementioned carbon dioxide depletion region at the oscillatory line of the spectrum and the 250 kHz frequency offset of peak amplification are similarly shifted.

In the operation of the spectrum analyzer of the invention, transmission of the radiation at a sequence of frequencies is initiated in the absence of the aforementioned chemicals or gaseous reagents to obtain a reference spectrum. A second transmission of the radiation at the same sequence of frequencies is initiated in the presence of the gaseous reagents. The transmissions of the radiation are directed toward a distant reflector from which echoes are obtained. The amplitude of echoes received at the respective frequencies for the first and the second transmissions provide data of attenuation introduced by the presence of the gaseous reagents. A set of equations in terms of attenuated echo amplitude for a set of transmission frequencies over a measured distance of propagation to the reflector is then solved for the individual concentrations of the respective gaseous reagents by use of a set of absorption coefficients of the gaseous reagents at the transmission frequencies.

BRIEF DESCRIPTION OF THE DRAWINGS

The aforementioned aspects and other features of the invention are explained in the following description taken in connection with the accompanying drawings wherein.

DESCRIPTION OF THE PREFERRED EMBODIMENT

Figure 1:
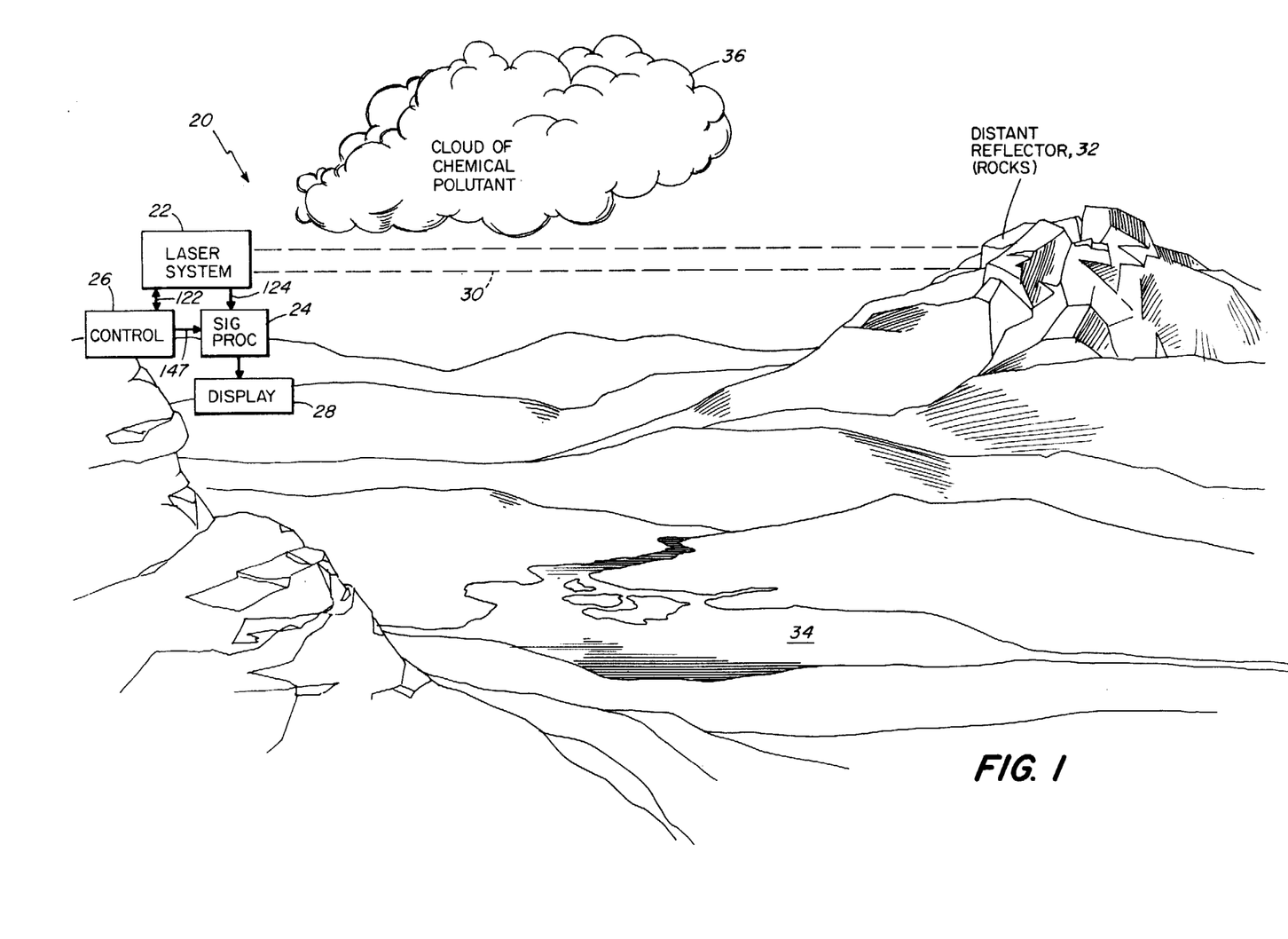
FIG. 1 is a stylized view of a laser spectrometer of the invention shown transmitting optical radiation toward a rocky portion of a hillside, a cloud of chemical reagents being seen approaching the path of the optical radiation.

Referring now to FIG. 1, a spectrometer system 20 of the invention comprises a laser system 22, a signal processor 24, a controller 26 and a display 28. The laser system 22 transmits optical radiation along a path 30 to a distant reflector 32, portrayed as a rock formation on a distant hillside, the optical radiation reflecting therefrom and propagating back along the path 30 to the laser system 22. The path 30 lies above a valley 34 through which a cloud 36 of airborne chemicals, such as a polluting insecticide, is traveling.

Initially, the optical path 30 propagates through clean air to the reflector 32 which, on occasion, may become occluded by haze or dust in the air. The dust in the air acts as a wide band attenuator of the portion of the infrared spectrum utilized in forming an identifying signature of the chemicals in the cloud 36. Accordingly, the laser system 22 is operative both before and during the presence of the cloud 36 in order to better determine the difference between the absorption spectra of the atmosphere plus any absorption of the rocks of the reflector 32 as compared to the absorption spectrum of the cloud 36. The controller 26 signals the laser system 22 for selecting sequentially the frequencies of the radiation transmitted along the path 30. The signal processor 24 stores a set of spectral absorption coefficients of the airborne chemicals as well as measured spectrograms of echoes reflected from the reflector 32 both before and during the presence of the cloud 36. The ratio of the echo amplitudes, at each frequency of transmitted radiation, observed both before and during the presence of the cloud 36, in conjunction with the range of the reflector 32 and the spectral absorption coefficients of the airborne chemicals, are utilized in computing the concentrations of the airborne chemicals. The resulting concentrations of the respective airborne chemicals are shown on the display 28.

Figure 2:
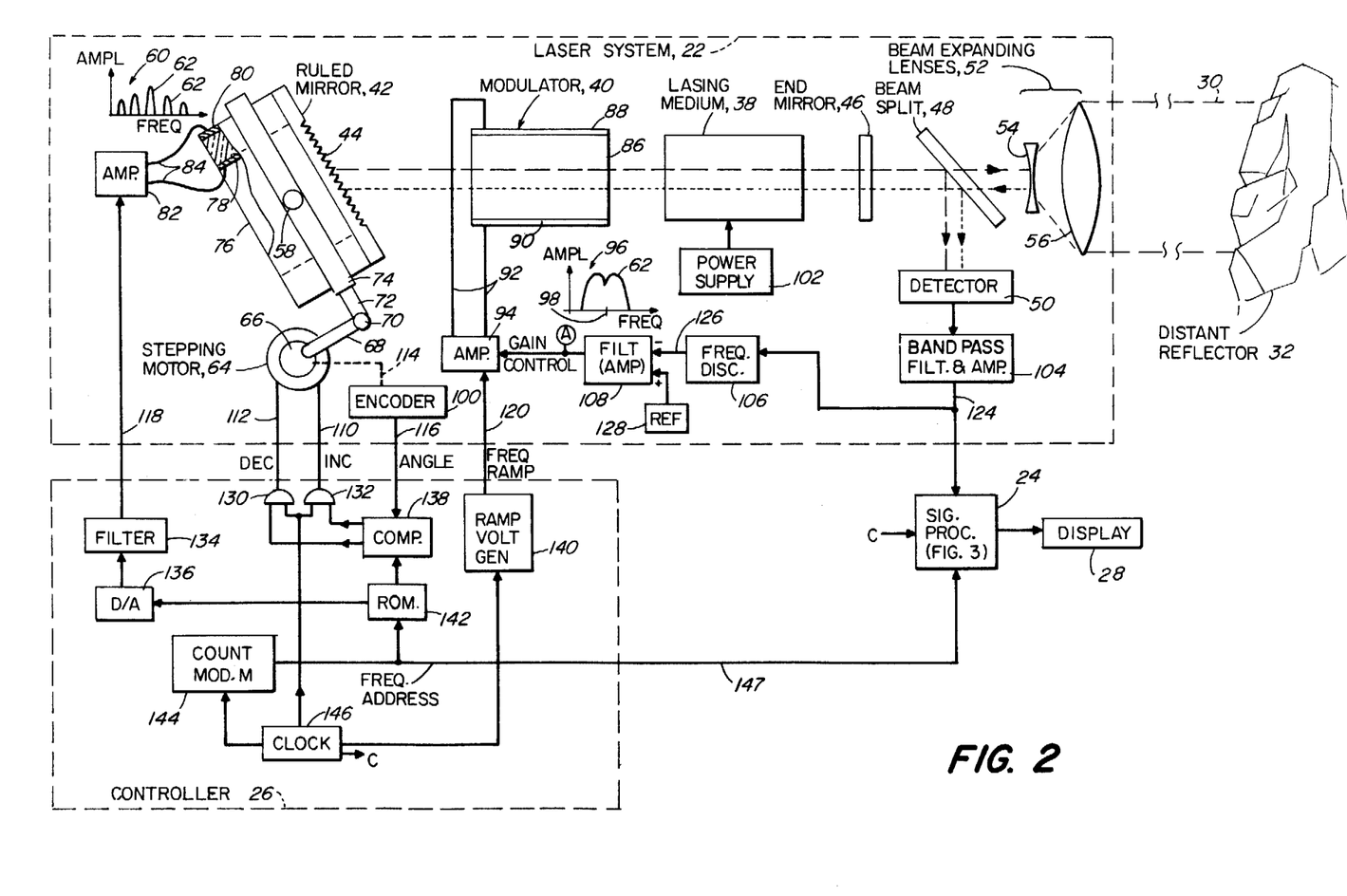
FIG. 2 is a detailed diagram of a laser system and control circuitry therefor referred to in FIG. 1.

Referring now to FIG. 2, the laser system 22 of FIG. 1 is seen to comprise a lasing medium 38, a modulator 40, a first end mirror 42 having an interferometric structure in the form of a grid line ruling 44 applied to the reflecting surface thereof, a second end mirror 46 which is partially transmissive to permit a portion of the radiation produced in the lasing medium 38 to propagate through the mirror 46 toward the reflector 32 of FIG. 1 as well as to permit radiation received from the reflector 32 to enter the lasing medium 38 for amplification therein, a beam splitter 48 for deflecting a portion of the radiation exiting from the mirror 46 to a detector 50, and a lens unit 52 having a concave lens 54 and a convex lens 56 for expanding the beam produced by the lasing medium 38. The first end mirror 42 is positioned along the axis of the lasing medium 38 with a normal to its reflecting surface oriented to the axis of the lasing medium 38 at an angle of approximately 20°. The mirror 42 is rotated about a pivot 58 for selecting successive ones of the bands of frequency wherein the lasing oscillations take place.

With reference to a graph 60 adjacent the mirror 42, individual bands 62 (five exemplary bands being shown though, in practice, many more bands are present) demonstrate the spectral regions wherein an oscillation of the laser system 22 can be produced. In particular, it is noted that each of the bands 62 is sufficiently wide to permit some variation in the lasing frequency so as to accommodate a frequency modulation of the radiation of the laser system 22, the aforementioned chirp frequency being confined to the bandwidth of a band 62.

The mirror 42 is rotated about the pivot 58 by a stepping motor 64 which is coupled by a crank 66 and a link 68. The link 68 is pivotably connected by a pivot 70 to an arm 72 extending from a brace 74 which supports the mirror 42 and includes the pivot 58. The stepping motor 64 includes a reduction gear (not shown) for driving the crank 66, the crank 66 being relatively short as compared to the distance between the pivots 58 and 70 to provide highly accurate rotation of the mirror 42 about a relatively small range of angles, typically 2°, which suffices to shift the oscillating frequency from one to another of the bands 62 in the spectrogram of the graph 60. The staircase appearance of the ruling 44 provides for an interferometric structure in which the grating lobes for each frequency of radiation are oriented at different angular orientations relative to a normal to the reflecting surface of the mirror 42. Orientation of the mirror 42 about the pivot 58 selects the specific lobe to be oriented along the optical axis of the lasing medium 38 so that a lasing frequency is obtained corresponding to the particular angle of orientation of the mirror 42. To further intensify the magnitude of the oscillation, the optical path length is finely adjusted by means of a piezoelectric crystal 76, of a material such as barium titanate, which has an annular shape and is secured within the brace 74 with the mirror 42 adhesively secured to the forward end of the crystal 76. The crystal has an inner electrode 78 and an outer electrode 80, seen in the cutaway view of the crystal 76, for imparting an electric field to the crystal. In the presence of the electric field, the mirror 42 is slightly displaced relative to the brace 74 for adjustment of the path length of the optical cavity of the laser system 22. An amplifier 82 applies a voltage via leads 84 to the electrodes 78 and 80 for impressing the aforementioned electric field.

In a preferred embodiment of the invention, carbon dioxide is utilized in the lasing medium 38 resulting in a nominal radiation wavelength of 10.6 microns. The bands 62 are approximately 50 MHz wide and spaced apart by approximately 50 gHz. The mirror 46 is composed of germanium so as to admit the propagation of the radiation therethrough, the partially reflecting surface of the mirror 46 reflecting most of the radiation back into the lasing medium 38 to maintain oscillation. The mirror 42 is composed of metal for reflecting all of the radiation back into the lasing medium 38. The modulator 40 comprises a cadmium telluride crystal 86 having its longitudinal axis coinciding with the axis of the lasing medium 38 so that the radiation propagates along the axis of the crystal 86. The modulator 40 includes electrodes 88 and 90 positioned on opposite sides of the crystal 86 and which are energized via leads 92 coupled to an amplifier 94 for imparting an electric field in a direction perpendicular to the propagation axis of the crystal 86. In response to variations in the electric field, the speed of propagation of the radiation through the crystal 86 is varied, the speed depending on the magnitude of the electric field. As will be explained hereinafter, the amplifier 92 provides a voltage and electric field wherein the amplitude varies linearly with time so that the propagation time through the crystal 86 also varies linearly with time. As a result, the optical length of the cavity of the laser system 22 is varied and a swept, or chirped, frequency of radiation results. At the frequency of oscillation within any one of the bands 62 of the graph 60, an enlarged view of one such band 62 being shown in the graph 66 adjacent the lasing medium 38, there is a depletion in the population of carbon dioxide molecules with a resultant loss in gain at the lasing frequency identified by point 98 of the graph 96. At a frequency offset at approximately 250 kHz to either side of the point 98, the amplifying gain of the lasing medium 38 is significantly higher. As will be seen hereinafter, the amount of the frequency offset imparted by the frequency modulation between the transmitted and received radiation frequencies is maintained equal to the aforementioned offset between the frequency at the amplification peak of the spectral band 62 and the lasing frequency at the point 98.

As seen in FIG. 2, the laser system 22 also comprises an angle encoder 100, a power supply 102, a bandpass filter 104 which includes an amplifier, a frequency discriminator 106 and a filter 108. The stepping motor 64 is driven forward or in reverse by clock pulse signals received from the controller 26 along lines 110 or 112 respectively for increasing or decreasing the angular orientation of the mirror 42. The encoder 100 is mechanically coupled to the motor 64 via line 114 and provides a digital electrical signal to the controller 26 via line 116 designating the angular orientation of the mirror 42. The controller 26 also transmits a signal along line 118 to the amplifier 82 for displacing the reflecting surface of the mirror 42. Also provided by the controller 26 is a signal along line 120 having a ramp voltage waveform, the ramp voltage on line 120 being amplified by the amplifier 94 to produce a ramp, or chirp, modulation to the radiation frequency. The lines 118, 112, 110, 116 and 120 are represented collectively by the line 122 in FIG. 1.

The beam splitter 48 is composed of germanium, as is the mirror 46, to permit the propagation of the infrared radiation therethrough, the beam splitter 48 being partially reflecting for directing the aforementioned portion of the radiation propagating along the axis of the lasing medium 38 toward the detector 50. The rays of radiation propagating toward the reflector 32 are portrayed by a dashed line while the rays of radiation which have returned to the laser system 22 from the reflector 32 are portrayed by a dotted line. Both a dashed line and a dotted line are seen to approach the detector 50 showing that both a reference beam having a radiation frequency equal to the present value of the frequency produced by the lasing medium 38 plus a received radiation beam having an earlier value of radiation frequency are applied to the detector 50. It is noted that the dotted line representing the received radiation is also shown within the lasing medium 38 to indicate the amplification of the received radiation. This is in accordance with a basic feature of the invention wherein the high amplification of an oscillating lasing medium is utilized for amplification of the received radiation signal. In a preferred embodiment of the invention, a mercury-cadmium-telluride amalgam is utilized for the material of the detector 50, the amalgam producing a voltage in accordance with the intensity of the sum of the wavefronts of the reference and received beams of radiation.

Due to the nonlinear interaction of the two wavefronts incident upon the detector 50, the electric signal produced by the detector 50 contains the difference frequency, or beat frequency component which is passed by the pass band of the band-pass filter 104, the filter 104 excluding other components of the heterodying action of the detector 50. The output signal of the filter 104 is coupled via line 124 to the signal processor 24 and to the frequency discriminator 106.

As was mentioned hereinabove, the lasing frequency is varied linearly in time so that, upon the return of the radiation signal from the reflector 32, the lasing frequency has shifted via the aforementioned 250 kHz so that a peak of the graph 96 is at the frequency of the received signal. In order to insure that the rate of frequency modulation produced by the modulator 40 is sufficiently fast to produce the aforementioned frequency shift during the round trip propagation time of radiation between the laser system 22 and the reflector 32, the discriminator 106 senses the magnitude of the frequency offset, this being equal to the beat frequency on line 124, and provides a signal on line 126 representing the magnitude of the frequency offset. The signal on line 126 is coupled via the filter 108 to the gain control terminal of the amplifier 94 for varying the gain of the amplifier 94, this, in turn, varying the magnitude of the ramp waveform on lines 92. The filter 108 is preferably in the form of an operational amplifier with a feedback loop which typically comprises a resistor-capacitor network to give an overall low pass filter characteristic to the filter 108, this ensuring stability of the feedback loop controlling the gain of the amplifier 94. A source 128 of reference voltage is applied to the positive input terminal of the amplifier of the filter 108 while the signal on line 126 is applied to the negative input terminal. Deviations from the desired offset frequency resulting from a directing of the path 30 of FIG. 1 to a nearer or further set of rocks on the hillside are compensated by the voltage on line 126 which drives the amplifier gain 94 in the proper sense to correct the frequency offset.

The controller 26 is seen to comprise two AND gates 130 and 132, a filter 134, a digital-to-analog converter 136, a comparator 138, a ramp voltage generator 140, a read-only memory 142, a counter 144 and a clock 146. The clock 146 provides timing signals for synchronizing the operation of the components of the laser system 22 with each other as well with the signal processor 24. Clock pulses from the clock 146 are coupled via terminal C to the processor 24 for operating the processor 24, via the AND gates 130 and 132 for operating the stepping motor 64, and to the counter 144. The clock 146 also transmits a timing signal to the generator 140 for initating a ramp voltage waveform produced by the generator 140.

The memory 142 stores angle data for the angle of orientation of the mirror 42 as well as displacement data for the displacement of the reflecting surface of the mirror 42 relative to the brace 74 for maximizing the power radiated by the laser system 22. The memory 142 is addressed by a count of the counter 144. Each address corresponds to a different band 62 of the graph 60 wherein an oscillation of the laser system 22 is to take place. In response to a clock pulse from the clock 146, the counter 144 increments its count by a value of one to address the next section of the memory 142 to provide the requisite orientation of the mirror 42 as well as the displacement of the reflecting surface thereof for oscillation at the corresponding frequency of radiation. In this way, in reponse to successive clock pulses from the clock 146, the laser system 22 radiates at a succession of frequencies within its spectrum of radiation.

Control of the orientation of the mirror 42 is accomplished by a feedback loop comprising the encoder 100, the comparator 138 and the two AND gates 130 and 132. The comparator 138 compares the digital signal of the memory 142 representing the desired angle of orientation with the signal on line 116 representing the actual angle of orientation. The comparator 138 then applies a digital signal having a logic state of 1 to the AND gate 132 or to the AND gate 130 depending respectively on whether the actual angle of orientation should be increased or decreased in order to equal the desired angle of orientation. When equality is attained, logic states of zero appear on both of the output lines of the comparator 138 so that no clock pulses of the clock 146 are communicated via the AND gates 130 and 132 to the motor 64. Simultaneously with the transmission of the requisite angle from the memory 142 to the comparator 138, the memory 142 also transmits the displacement data to the converter 136 which converts the digital signal of the memory 142 to an analog signal, the analog signal, in turn, being coupled by the filter 134 to line 118 for adjusting the displacement of the mirror 42. The filter 134 is typically a low pass filter for ensuring a smooth transition in the displacement of the reflecting surface of the mirror 42.

The ramp voltage waveform on line 120 is produced by the generator 140 in response to the aforementioned triggering thereof by the clock 146. If desired, the generator 140 may be triggered simultaneously with each triggering of the counter 144 or, alternatively, the generator 140 may be permitted to produce a longer duration ramp waveform such as to encompass a time interval sufficient for several counts of the counter 144. The address represented by the counter 144 is also coupled from the counter 144 via line 147 to the processor 24 to indicate which frequency of oscillation is being produced by the laser system 22.

In operation, therefore, the lasing medium 38 is excited by electric power from the power supply 102 to a sufficient level to produce oscillation of the laser system 22. The frequency of oscillation is determined by the spacing between the reflecting surfaces of the mirrors 42 and 46, as well as the orientation of the mirror 42 with its stair case ruling 44, the orientation setting the projected height of steps of the staircase upon the optical axis of the lasing medium 38. In response to signals of the memory 142, the orientation of the mirror 42 is adjusted to select a specific band 62 of the graph 60 wherein an oscillation is produced, the magnitude of the power of the radiation transmitted by the laser system 22 being maximized by adjustment of the displacement of the reflecting surface of the mirror 42 in accordance with signals of the memory 142. Successive bands 62 for oscillation are selected by counts of the counter 144 in response to a pulsing of the counter by the clock 146. In synchronism with the pulsing of the counter 144, the clock 146 also activates the generator 140 to produce a voltage with a ramp waveform whereby the modulator 40 linearly modulates the frequency of oscillation within the selected band 62. The rate of frequency modulation is adjusted by the discriminator 106 in conjunction with the variable gain characteristic of the amplifier 94 to produce a fixed beat frequency on line 124 independently of the distance of the reflector 32 from the lens unit 52. Thereby, the reflected radiation is passed through the same lasing medium 38 which is utilized for producing the transmitted radiation, and has its frequency offset from that of the transmitted radiation by an amount which corresponds to the location of a peak of the band 62 in the graph 96 for maximum amplification of the received signal. The amplified received signal and a portion of the transmitted signal which serves as a reference signal are summed together and detected by the detector 50 to produce a signal on line 124. The amplitude of the signal on line 124 varies in accordance with the absorption spectra of chemicals located within the optical path 30.

By way of alternative embodiments of the lasing system 22, it is noted that the interferometric structure of the ruling 44 may be inplemented by utilizing a transparent plate of germanium with rulings thereon (not shown) which is displaced from the axis of the medium 38 and inclined therewith. In this alternative embodiment the mirror 42 would be replaced with a mirror (not shown) oriented at an angle to the axis of the medium 38 for directing radiation from the plate along the axis of the medium 38. The amplifier 82 and crystal 76 would be utilized for adjusting the position of the reflecting surface of the mirror while the stepping motor 64 would be utilized for adjusting the orientation of the interferometric structure.

Figure 3:
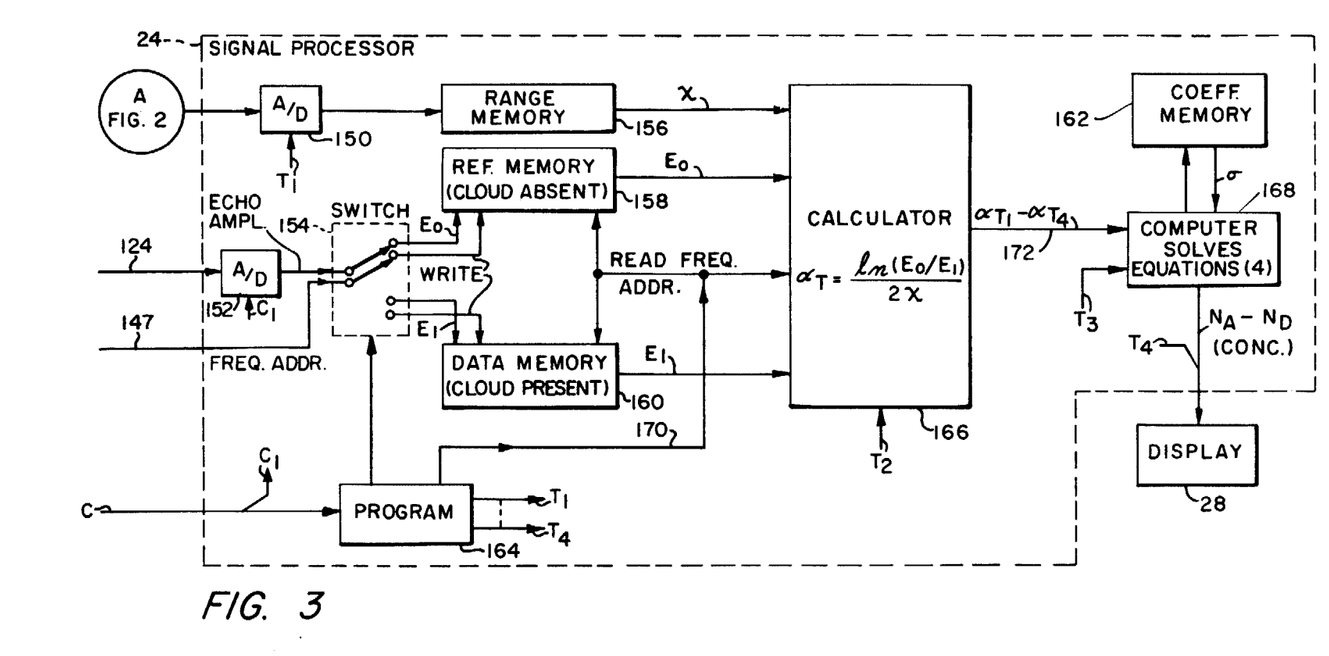
FIG. 3 is a block diagram of a signal processor of FIG. 1 which computes concentrations of chemical reagents.

Referring now to FIG. 3, the signal processor 24 is seen to comprise analog-to-digital converters 150 and 152, a switch 154, four memories 156, 158, 160 and 162, a programmer 164, a calculator 166, and a computer 168. The signal on line 124 of FIG. 1 is converted from an analog format to a digital format by the converter 152 in response to clock pulses at terminal C1 provided by the clock 146 of FIG. 2. Thus, the output signal of the converter 152 consists of digital samples of the amplitude of the echo signal provided by the band pass filter 104 of FIG. 2. Both the signal at the output of the converter 152 and the frequency address on line 147 are applied to the switch 154 for coupling either to the memory 158 or to the memory 160. The signal on line 147 also serves as the address for writing in data from the converter 152 into the memories 158 and 160. Since the signal on line 147, as noted hereinabove with reference to FIG. 2, designates the specific frequency at which the laser system 22 is transmitting, the memories 158 and 160 store data of echo amplitudes as a function of the frequency of transmission of the laser system 22.

The signal at terminal A, at the output of the filter 108 of FIG. 2, is applied to the converter 150 for converting this signal from an analog format to a digital format. As was noted hereinabove, the signal at terminal A varies in amplitude in accordance with the round trip propagation time of optical signals propagating between the laser system 22 and the reflector 32. Accordingly, the amplitude of the signal at terminal A is a measure of the round-trip distance between the lenses 52 and the reflector 32. The programmer 164 in response to clock pulse signals from terminal C of the clock 146 provides timing signals at terminals T1-T4, the signal at terminal T1 serving to strobe the converter 150 for the storing of a digital signal in the memory 156, the stored signal representing the round-trip distance between the lenses 52 and the reflector 32, the distance being shown in FIG. 3 by the symbol x. The round-trip distance will be utilized in a manner, to be described hereinafter, by the calculator 166 for calculating attenuation factors resulting from the chemicals in the cloud 36 of FIG. 1. Similarly, the signals stored in the memories 158 and 160, in response to a read command signal on line 170 from the programmer 164, provide data of stored echo amplitudes which are utilized by the calculator 166, in a manner to be described, for the calculation of attenuation factors.

The attenuation factors are coupled from the calculator 166 via line 172 to the computer 168 which solves a set of equations, to be described hereinafter, relating to attenuations measured at corresponding frequencies of the radiation to derive the concentrations of the respective chemicals of the cloud 36. The memory 162 stores values of attenuation cross sections, $\sigma$, of the respective chemicals which are known at the frequencies at which the laser system 22 radiates. The values of $\sigma$ appear in the equations utilized by the computer 168 in producing the respective values of concentration of the chemicals for presentation of the display 28. Timing signals T2-T4 of the programmer 54 are applied respectively to the calculator 166, the computer 168 and the display 28 for synchronizing their respective operations.

Figure 4:
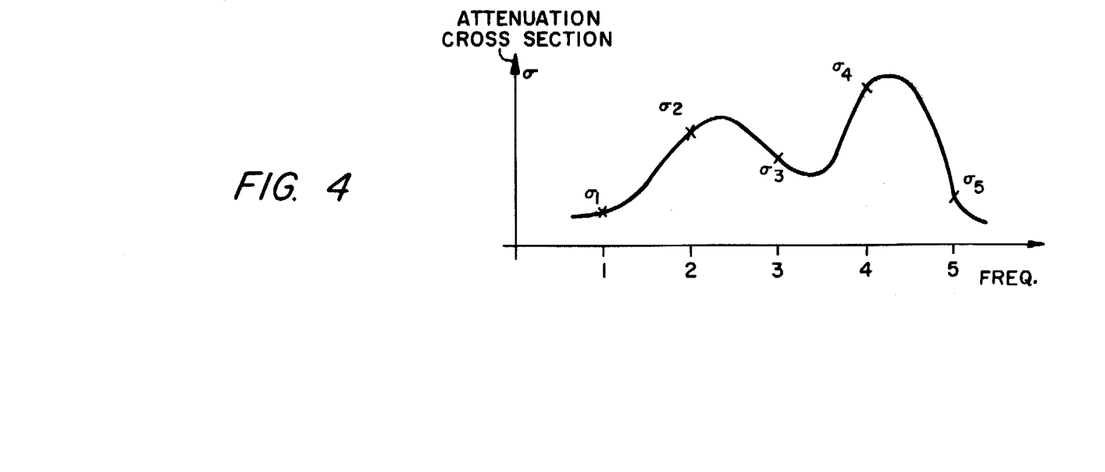
FIG. 4 is an exemplary sampled absorption spectrum of a chemical reagent of the cloud.

Referring also to FIG. 4, there is shown an exemplary graph of the attenuation cross section, $\sigma$, as a function of frequency for one of the chemicals of the cloud 36, the values of $\sigma$ being shown on the vertical axis and the values of frequency being shown on the horizontal axis. The value of $\sigma$ is seen to vary with frequency and, accordingly, five exemplary values identified by $\sigma_1-\sigma_5$ are shown corresponding to five exemplary values of frequency. Other chemicals are described by similar graphs of attenuation cross section. Spectroscopic data such as attenuation cross section are known for the types of chemicals which may be present in the cloud 36 of FIG. 1. With respect to the values of $\sigma$ stored in the memory 162, the values are stored for each of the chemicals as a function of the frequencies at which the laser system 22 is to radiate. The resulting attenuation factors, to be more fully described hereinafter, are proportional to the value of $\sigma$ and to the concentration of the chemical.

The operation of the signal processor 24 of FIG. 3 may be better understood by considering the following equations relating to the attenuation factors describing the attenuation of the optical signal by the chemicals in the cloud 36. The intensity of the echo signal incident upon the detector 50 of FIG. 2 is proportional to the product of two exponential terms, the first term having an attenuation factor resulting from the effects of the ambient dust and water in the air, and the second term having an attenuation factor resulting from the effects of the chemical pollutants of the cloud 36. Thus, the second exponential term represents the ratio of the intensity of an echo received in the presence of the cloud 36 to the intensity of an echo received in the absence of the cloud 36. As will be seen with reference to the ensuing equations, the concentrations of the respective chemicals can be determined by measurements of the foregoing ratio of echo intensities at each of a set of frequencies, the number of frequencies at which the measurements are made being equal to the number of chemicals suspected as being in the cloud. Rewriting the aforementioned exponential term, $\alpha$, the attenuation factor is given by $$\alpha = (1/x)\ln(I_0/I_1) = (2/x)\ln(E_0/E_1) \qquad (1)$$

where x is the round trip distance; $I_0$ and $E_0$ are the intensity and amplitude, respectively, of the optical signal echo in the absence of the polluting chemicals; and $I_1$ and $E_1$ are the intensity and amplitude, respectively, of the optical signal echo in the presence of the polluting chemicals.

The relationship expressed by Equation 1 applies at each frequency of transmission by the laser system 22 of FIG. 2. The round trip distance, x, is initially measured when the reflector 32 is selected and, thereafter, remains constant. The values of $I_0$ and $E_0$ are initially measured at each of the transmission frequencies prior to the appearance of the cloud 36 of FIG. 1, the programmer 164 of FIG. 3 positioning the switch 154 for directing the storage of the values of $E_0$ at the respective frequencies in the memory 158. Later, after the arrival of the cloud 36, the programmer 164 positions the switch 154 for coupling the echo amplitude data from the converter 152 to the memory 160 whereupon the values of $E_1$ are stored in correspondence with the transmission frequencies in the memory 160. The values of x, $E_0$ and $E_1$ are then utilized by the calculator 166 to calculate the corresponding values of $\alpha$, it being appreciated that different values of $\alpha$ are obtained for different values of transmission frequency and for different concentrations of the chemicals in the cloud 36.

With reference to the operation of the detector 50 of FIG. 2, such detectors are nonlinear devices and produce electrical signals proportional to the product of the reference and echo signals incident thereupon. One term of the product, known as the cross product term, results in the difference frequency which is extracted by the bandpass filter 104. The amplitude of the cross product term is proportional to the amplitude of the reference signal and to the amplitude of the echo. In view of the fact that the amplitude of the reference signal is maintained constant, the amplitude of the difference frequency signal on line 124 is thus seen to be dependent only on the amplitude of the echo signal. Thus, it is seen that, in the event that only one signal were present, the signal produced by the detector 50 would be proportional to the intensity of the incoming optical signal, but as in the present case where both the reference signal and the echo signal are present, the cross product term produces the aforementioned signal on line 124 which has an amplitude directly proportional to the amplitude of the optical signal rather than its intensity. Since the intensity of an optical signal is proportional to the square of its amplitude, Equation 1 shows $\alpha$ both in terms of the intensity and in terms of the amplitude of the echo signal, the factor of 2 in the right hand portion of the equation entering by virtue of the aforementioned relationship of squared amplitude and intensity.

While the number of chemical pollutants in the cloud 36 may be unknown prior to the measurement of the respective concentrations, by way of example in explaining the operation of the signal processor 24, it is assumed that there may be four chemicals present in unknown concentrations. The four chemicals will be identified in the ensuing equations by the letters A, B, C and D, these letters appearing as subscripts for identifying the respective attenuation cross sections, $\sigma$, the concentration in terms of the number, N, of milligrams of chemical per cubic meter, and the attenuation factors $\alpha$, for the respective chemicals.

With reference to the set of equations $$\alpha_{A1} = N_A \sigma_{A1}$$

$$\alpha_{A2} = N_A \sigma_{A2}$$

$$\alpha_{A3} = N_A \sigma_{A3}$$

$$\alpha_{A4} = N_A \sigma_{A4} \tag{2}$$

the subscript A identifies the first of the chemicals while the subscripts 1–4 identify the respective frequencies. The four values of $\sigma$ appearing in the set of Equations 2 correspond to the first four values of $\sigma$ in the graph of FIG. 4. Each of the Equations (2) expresses the attenuation factor for $\alpha$ at each frequency in terms of the attenuation cross section, $\sigma$, at that frequency and in terms of the unknown concentration, $N_A$, of the first of the chemicals. A similar set of equations with subscript B describes the attenuation constants $\alpha_{B1}$–$\alpha_{B4}$ for the chemical B, with corresponding sets of equations being utilized for other chemicals such as the chemicals C and D.

When more than one chemical is present in the cloud 36, as is the case with the present example of four chemicals, the attenuation factor, represented by $\alpha_T$, is equal to the total contribution of the attenuation constants of the respective chemicals A–D. This relationship is expressed in the set of equations $$\alpha_{T1} = \alpha_{A1} + \alpha_{B1} + \alpha_{C1} + \alpha_{D1}$$

$$\alpha_{T2} = \alpha_{A2} + \alpha_{B2} + \alpha_{C2} + \alpha_{D2}$$

$$\alpha_{T3} = \alpha_{A3} + \alpha_{B3} + \alpha_{C3} + \alpha_{D3}$$

$$\alpha_{T4} = \alpha_{A4} + \alpha_{B4} + \alpha_{C4} + \alpha_{D4} \tag{3}$$

wherein the subscripts 1–4 indicate the respective transmission frequencies of the laser system 22 at which the attenuation measurements are made. The values of the attenuation constants $\alpha_{A1}$–$\alpha_{A4}$ are given by Equations (2) with similar sets of equations defining the values of the attenuation constants $\alpha_{B1}$–$\alpha_{D4}$. Substituting the values of Equation (2) as well as the corresponding values of the equations of the chemicals B–D for the terms $\alpha_{A1}$–$\alpha_{D4}$ in Equations (3) produces the set of equations $$\alpha_{T1} = N_A \sigma_{A1} + N_B \sigma_{B1} + N_C \sigma_{C1} + N_D \sigma_{D1}$$

$$\alpha_{T2} = N_A \sigma_{A2} + N_B \sigma_{B2} + N_C \sigma_{C2} + N_D \sigma_{D2}$$

$$\alpha_{T3} = N_A \sigma_{A3} + N_B \sigma_{B3} + N_C \sigma_{C3} + N_D \sigma_{D3}$$

$$\alpha_{T4} = N_A \sigma_{A4} + N_B \sigma_{B4} + N_C \sigma_{C4} + N_D \sigma_{D4} \tag{4}$$

wherein the four values of attenuation constant, $\alpha_{T1}$–$\alpha_{T4}$, are given in terms of known values of $\sigma$ and the four unknown concentrations, $N_A$–$N_D$, of the four chemicals. With reference also to FIG. 3, the values of $\alpha_{T1}$–$\alpha_{T4}$ are provided by the calculator 166 while the values of the coefficients, $\sigma_{A1}$–$\sigma_{D4}$ are provided by the memory 162. The programmer 164 of FIG. 3, as noted hereinbefore, provides the read address for reading out the values $E_0$ and $E_1$ at each of the transmission frequencies to permit the calculator 166 to calculate the values of $\alpha_T$ for each of the transmission frequencies. The coupling of the values of $\alpha_{T1}$–$\alpha_{T4}$ to the computer 168 and the operation of the computer 168 are accomplished under direction of the timing signals T2 and T3 of the programmer 64. Thus, the set of Equations (4) is presented to the computer 168 which then solves the four equations for the four unknown concentrations $N_A$–$N_D$ and presents the values of the concentrations to the display 28.

It is understood that the above-described embodiment of the invention is illustrative only and that modifications thereof may occur to those skilled in the art. Accordingly, it is desired that this invention is not to be limited to the embodiment disclosed herein but to be limited only as defined by the appended claims.

What is claimed is:

1. A laser spectrometer comprising:
   a lasing medium;
   first and second reflecting means positioned at opposite ends of said lasing medium, said first reflecting means including interferometer means for selecting a single oscillatory band of a set of oscillatory bands of said lasing medium;
   means for directing radiation produced by said lasing medium through a region of space having material to be analyzed, said radiation propagating through said region back to said lasing medium to provide an amplified received radiation signal;
   means for altering a frequency of oscillation of said lasing medium prior to the return to said lasing medium of said radiation from said region for maximizing the amplification of said received radiation signal;
   means coupled to said first reflecting means to produce a succession of radiations each of which has a specific frequency of oscillation; and
   means coupled to said lasing medium for combining data of individual ones of said radiation signals received prior to the entry of said material into said region with data of individual ones of said radiation signals at corresponding frequencies received subsequent to the entry of said material into said region to provide a measure of the concentration of said material.

2. A spectrometer according to claim 1 wherein said first reflecting means further comprises means for altering the length of an optical path passing through said lasing medium.

3. A spectrometer according to claim 1 further comprising a modulator positioned along an optical path threading said lasing medium for varying the frequency of oscillation of said radiation as a function of time.

4. A spectrometer according to claim 1 further comprising means connected between said lasing medium and said combining means for extracting a signal at a frequency equal to the difference between the frequency of said received signal and the frequency of radiation produced by said lasing medium subsequent to said altering of frequency.

5. A spectrometer according to claim 4 wherein said succession producing means includes a memory providing control signals to said interferometer means, and means for sequentially addressing said memory for said specific frequencies of oscillation in said succession of radiations.

6. A spectrometer according to claim 1 wherein said frequency altering means includes means for heterodyning a received radiation signal with a reference radiation signal, means for signaling the magnitude of a beat frequency resulting from said heterodyning, and means coupled between said heterodyning means and said beat frequency signaling means for adjusting the amount of altering of said frequency of oscillation to produce a predetermined frequency offset.

7. A laser spectral measurement system comprising:
a lasing medium;
first and second reflecting means positioned at opposite ends of said lasing medium, said first reflecting means including interferometer means for selecting a single oscillatory band of a set of oscillatory bands of said lasing medium;
means for directing radiation produced by said lasing medium through a region of space having material to be analyzed, said radiation propagating through said region back to said lasing medium to provide an amplified received radiation signal;
means for altering a frequency of oscillation of said lasing medium prior to the return to said lasing medium of said radiation from said region for maximizing the amplification of said received radiation signal;
means coupled to said first reflecting means to produce a succession of radiations each of which has a specific frequency of oscillation; and
means coupled between said succession producing means and said lasing medium for measuring the concentration of a component of said material of said region of space.

8. A system according to claim 7 wherein said concentration measurement means comprises means responsive to said received radiation signal for measuring an attenuation factor thereof, said attenuation factor being utilized in deriving said concentration.

9. A system according to claim 8 wherein said concentration measurement means further comprises means responsive to said received radiation signal for measuring the distance travelled by said radiation through said region of space.

10. A system according to claim 9 wherein said concentration measurement means includes means responsive to said attenuation factor and said distance travelled by said radiation for computing a value of said concentration.

11. A system according to claim 8 wherein said attenuation measurement means is responsive to a signal of said succession producing means for providing values of attenuation factors dependent on the values of the frequencies of said oscillations.

12. A laser measurement system comprising:
a laser having a lasing medium and reflecting means for reflecting optical radiation within said medium, said reflecting means being adjustable for selecting a frequency of oscillation of said laser;
means for directing radiation transmitted by said lasing medium to a reflector distant from said laser, said directing means including means for directing radiation reflected from said reflector back through said lasing medium to provide amplification of said reflected radiation; and
means coupled to said laser for adjusting said reflecting means to offset said frequency of oscillation from that of said reflected radiation to maximize said amplification, said adjusting means being responsive to the range of said reflector for altering said frequency of oscillation prior to the return to said lasing medium of radiation reflected by said reflector.

13. A system according to claim 12 wherein said adjusting means includes means for generating a ramp signal to vary said frequency of oscillation at a predetermined rate, and means coupled to said directing means for comparing the frequency of said transmitted radiation with the frequency of said reflected radiation, said ramp generating means being coupled to said comparing means to provide said predetermined rate with a magnitude proportional to the difference in frequency between the frequencies of said transmitted and said reflected radiation.

* * * * *